(12) United States Patent
Schreiber (10) Patent No.: US 9,616,131 B2
(45) Date of Patent: Apr. 11, 2017

(54) PERFLUORCARBON NANOEMULSIONS WITH ENDOCYTOSIS ENHANCING SURFACE FOR GENE-TRANSFER

(75) Inventor: Sören Schreiber, Hattingen (DE)

(73) Assignee: SOLUVENTIS UG (DE)

( * ) Notice: Subject to any disclaimer, the term of this patent is extended or adjusted under 35 U.S.C. 154(b) by 448 days.

(21) Appl. No.: 12/992,280

(22) PCT Filed: May 13, 2009

(86) PCT No.: PCT/EP2009/055779
§ 371 (c)(1),
(2), (4) Date: Dec. 17, 2010

(87) PCT Pub. No.: WO2009/141257
PCT Pub. Date: Nov. 26, 2009

(65) Prior Publication Data
US 2011/0091561 A1 Apr. 21, 2011

(30) Foreign Application Priority Data
May 19, 2008 (EP) .................... 08156434

(51) Int. Cl.
*A61K 47/24* (2006.01)
*A61K 9/107* (2006.01)
*A61K 38/40* (2006.01)

(52) U.S. Cl.
CPC ............ *A61K 47/24* (2013.01); *A61K 9/1075* (2013.01); *A61K 38/40* (2013.01)

(58) Field of Classification Search
CPC ...... A61K 38/40; A61K 47/24; A61K 9/1075; C12Q 1/6886; C12Q 2600/154
See application file for complete search history.

(56) References Cited

U.S. PATENT DOCUMENTS

| 6,071,890 A | 6/2000 | Scheule et al. |
| 7,211,248 B2 | 5/2007 | Davidson |

| 2002/0155084 A1* | 10/2002 | Roessler et al. |
| 2004/0115159 A1 | 6/2004 | Tadlock et al. |
| 2006/0013820 A1 | 1/2006 | Bonnet et al. |
| 2007/0184076 A1 | 8/2007 | Unger et al. |

FOREIGN PATENT DOCUMENTS

| AU | 2009249812 A1 | 11/2009 |
| CA | 2725513 A1 | 11/2009 |
| CN | 102112109 A1 | 6/2011 |
| EP | 0 788 347 | 12/1995 |
| EP | 0 831 770 | 12/1996 |
| EP | 1 306 083 | 5/2003 |
| EP | 1 844 772 | 10/2007 |
| EP | 2123256 A1 | 11/2009 |
| EP | 2285349 A1 | 2/2011 |
| JP | H 11 508237 | 7/1999 |
| JP | 2001 002592 | 1/2001 |
| JP | 2011520936 A | 7/2011 |
| WO | 96 40053 | 12/1996 |
| WO | 96 40057 | 12/1996 |
| WO | 2009 141257 A1 | 11/2009 |

OTHER PUBLICATIONS

Gu, Xiping, et al; "Research progress of transferrin as an active targeting carrier"; Chinese Pharmaceutical Journal, vol. 40, Issue 8, pp. 568-571; Apr. 2005 (article and partial English translation provided).

Qian et al, "Targeted drug delivery via the transferrin receptor-mediated endocytosis pathway"; Pharmacol. Rev. 54; 2002; pp. 561-587.

Zhong et al; "Characterization of Transferrin-Modified Procationic-Liposome Protamine-DNA Complexes"; Yakugaku Zasshi 127 (3), pp. 533-539; 2007 The Pharmaceutical Society of Japan.

Truong-Le, et al; "Controlled Gene Delivery by DNA-Gelatin Nanospheres"; Human Gene Therapy 9:1709-1717, Aug. 10, 1998.

Mao et al; "Chitosan-DNA nanoparticles as gene carriers: synthesis, characterization and transfection efficiency"; Journal of Controlled Release 70 (2001) pp. 399-421.

\* cited by examiner

*Primary Examiner* — Snigdha Maewall (57) ABSTRACT

The present invention provides stable perfluorcarbon nanoemulsions with endocytosis enhancing surfaces that are suitable for gene-transfer, its production and use.

4 Claims, 11 Drawing Sheets

SEQUENCE LISTING

```
<160> NUMBER OF SEQ ID NOS: 1

<210> SEQ ID NO 1
<211> LENGTH: 21
<212> TYPE: DNA
<213> ORGANISM: Artificial
<220> FEATURE:
<223> OTHER INFORMATION: angiotensinogen siRNA

<400> SEQUENCE: 1
ccggttcttg ccactgagaa a                                                 21
```

PERFLUORCARBON NANOEMULSIONS WITH ENDOCYTOSIS ENHANCING SURFACE FOR GENE-TRANSFER

This application is a 371 of PCT/EP2009/055779, filed May 13, 2009, which claims foreign priority benefit under 35 U.S.C. §119 of the European Patent Application No. 08156434.6 filed May 19, 2008.

The present invention provides stable perfluorcarbon nanoemulsions that are suitable for gene-transfer, its production and use.

INTRODUCTION

Conventional oligonucleotides and more recently short interfering RNAs are promising and widely used materials for gene transfer. Until now, the possibilities to apply this genetic material to a living animal are very limited.

For the delivery of genetic material, perfluorcarbon (PFC) emulsions are a promising tool, as these emulsions are successfully used as oxygen transporters (Daugherty, W. P., et al., Neurosurgery 54:1223-1230 (2004); Riess, J. G., Artif. Cells Blood Substit. Immobil. Biotechnol. 33:47-63 (2005)). Following intratracheal application, conventional perfluorcarbon emulsions can transport drugs into the lung (Dickson, E. W. et al., Acad. Emerg. Med. 10:1019-1023 (2003)). Moreover, PFC emulsions have the advantage of a safe elimination by exhalation (Putyatina, T. K. et al., Artif. Cells Blood Substit. Immobil. Biotechnol. 22:1281-1285 (1994)).

Therefore, perfluorcarbons could function as an effective and safe tool for the delivery of genetic material into a living animal. Due to their function as oxygen trans-porters conventional PFC-emulsions have seizes that prevent leaving the vascular bed and therefore such emulsions would not be able to transport substances into cells of a living organism. Several less effective transport systems e.g. transport bound to cholesterol or mediated by apoliprotein A into the liver (Kim, S. I. et al., A-I. Mol. Ther. 15:1145-1152 (2007)) have been presented in the last years.

EP-B-0788347 discloses the production of water-in-oil fluorocarbon emulsion containing aqueous droplets of an average diameter of up to 10 nm. A fluorinated tenside or a mixture of tensides containing at least one fluorinated tenside is utilized as emulsifying agent.

EP-A-1844772 discloses a composition for transfection of cells with oligonucleotides wherein the emulsifying agent is an imidazolium derivative having $C_{10}$-$C_{36}$ hydrocarbon or fluorocarbon chains.

EP-B-00831770 discloses a continuous microdispersion of fluorinated compounds containing a discontinuous phase carrying the pharmaceutically active compound.

US 2004/0115159 discloses an oil-in-water nanoemulsion consisting of a ternary system of surface active substances that is suitable as a transport agent for cosmetics and pharmaceutical agents. This ternary system comprises an anionic, cationic and an amphiphilic surfactant.

U.S. Pat. No. 7,211,248 discloses methods for transfection of liver cells with DNA in which an ultrasonic contrast agent is supplemented with a protein stabilizing microparticle carrying plasma DNA. Transfection is effected by ultrasonication of liver cells.

US 2007/0184076 discloses a mixture of nanodrops consisting of biologically acceptable oil mixture of fluorcarbons and a therapeutically active substance, e.g. an anti-cancer agent.

US 2006/0013820 discloses a composition comprising various fluorcarbons, an antigen that is suitable as therapeutic agents, and optionally additional pharmaceutical carriers. The composition is said to be suitable as a vaccine especially for treating of HIV.

WO 96/40057, WO 96/40053 and EP-A-1306083 disclose stable perfluorcarbon (nano)emulsion as carriers for therapeutically active substances.

U.S. Pat. No. 6,071,890 discloses amphiphilic cationic substances supporting the transport of DNA and RNA and further biologically active compounds within the body. These substances are coupled to steroids.

WO 01/722812 discloses a microparticles comprising a polymeric material, a biologically active therapeutic factor and lipid proteins as transfection agents.

A reliable transport vehicle for gene transfer in an organism is still required.

SUMMARY OF THE INVENTION

It was now found that a perfluorcarbon nanoemulsion, notably a perflourcarbon nanoemulsion that has phospholipids as emulsifying agents, which has an endocytosis enhancing surface is suitable for the application of genetic material in vivo. The addition of molecules that provide an endocytosis enhancing surface to the nanoemulsion significantly augments the uptake of the perfluorcarbon nanoemulsion into cells. The invention thus provides (1) a stable perfluorcarbon nanoemulsion having an endocytosis enhancing surface;

(2) a preferred embodiment of (1) above, wherein said nanoemulsion has a continuous perfluorcarbon phase and a buffered discontinuous aqueous phase and comprises (a) a perfluorcarbon component comprising at least one least one perfluorcarbon compound;

(b) an emulsifying component; and (c) an endocytosis enhancing component comprising at least one compound inducing cellular uptake of the nanoemulsion via endocytosis;

(3) a gene-transfer agent or a pharmaceutical composition comprising the nanoemulsion as defined in (1) or (2) above, (4) a method for preparing the nanoemulsion of (1) or (2) above, or the gene-transfer agent or pharmaceutical composition of (3) above, which comprises the following steps (a) preparing a buffered aqueous solution containing the emulsifying component, (b) adjoining the perfluorcarbon component, and (c) mixing and homogenizing by a high pressure homogenizer of the reaction product of step (b);

(5) the use of a nanoemulsion as defined in (1) or (2) above for preparing a medicament for transferring genetic material to a patient;

(6) a method for transferring genetic material to a patient, which comprises administering a patient a nanoemulsion as defined in (1) or (2) above or a gene-transfer agent or a pharmaceutical composition as defined in (3) above; and (7) a method for transferring hydrophilic compounds to cells in vitro, which comprises contacting the cells with a nanoemulsion as defined in (1) or (2) above or with the gene-transfer agent as defined in (3) above.

SHORT DESCRIPTION OF THE FIGURES

FIG. 1 shows the temperature profile of the heating unit and the mean body temperature with standard deviation of five anaesthetized mice.

FIG. 2 shows the mean arterial blood pressure with standard deviation of five anaesthetized mice during the cooling sequence (control).

DETAILED DESCRIPTION OF THE INVENTION

The stable perfluorcarbon nanoemulsion of aspect (1) or (2) of the invention (hereinafter shortly referred to as "nanoemulsion of the invention") has a continuous perfluorcarbon phase and a buffered discontinuous aqueous phase. It is preferred that the buffered aqueous phase corresponds to 25 to 60 wt. % of the nanoemulsion. Suitable buffers for the aqueous phase include phosphate buffers such as sodium dihydrogenphosphate.

The nanoemulsion of the invention is a nanoemulsion, which means that it has a particle size of below 100 nm. It is preferred that the nanoemulsion of the invention consists of particles having an average size of about 50 nm.

The nanoemulsion of the invention is comprised of a perfluorcarbon component (a) comprising at least one least one perfluorcarbon compound, an emulsifying component (b) that preferably comprises phospholipids as the essential emulsifying compound and that may further comprise helper lipids, and an endocytosis enhancing component (c) that comprises at least one compound inducing cellular uptake of the nanoemulsion.

The at least one perfluorcarbon compound of component (a) is preferably selected from compounds having the structure
$C_mF_{2m+1}X$, $XC_mF_{2m}X$, $XC_nF_{2n}OC_oF_{2o}X$, $N(C_oF_{2o}X)_3$ and $N(C_oF_{2o+1})_3$,
wherein m is an integer from 3 to 10, n and o are integers from 1 to 5, and X is independently from further occurrence selected from Cl, Br and I.

The component (a) may contain a mixture of said perflourcarbon compounds. Particularly preferred perfluorcarbon compounds are perfluoroocytlbromide and perfluorotributylamine and mixtures thereof.

The emulsifying component (b) may comprise a great variety of emulsifying compounds known in the art, notably that disclosed in the references cited in the introduction. Preferred emulsifying compounds are phospholipids, even more—as set forth above—it is particularly preferred that phospholipids are the essential emulsifying compound of the emulsifying component (b). Thus, the emulsifying component (b) preferably comprises at least one phospholipid compound represented by the formula I wherein
$R^1$ und $R^2$ are independently selected from H and $C_{16-24}$ acyl residues, which may be saturated or unsaturated and may carry 1 to 3 residues $R^3$ and wherein one or more of the C-atoms may be substituted by O or $NR^4$, and
X is selected from H, $-(CH_2)_p-N(R^4)_3^+$, $-(CH_2)_p-CH(N(R^4)_3^+)-COO^-$, $-(CH_2)_p-CH(OH)-CH_2OH$ and $-CH_2(CHOH)_p-CH_2OH$ (wherein p is an integer from 1 to 5;
$R^3$ is independently selected from H, lower alkyl, F, Cl, CN und OH; and
$R^4$ is independently selected from H, $CH_3$ und $CH_2CH_3$
or a pharmacologically acceptable salt thereof.

In the above structure it is preferred that $R^1$ und $R^2$ are independently selected from H and unsubstituted $C_{16-24}$ acyl residues, which may be saturated or unsaturated, and X is selected from a choline, serine, ethanolamine and inositol residue. Most preferred the phospholipid component is selected from phosphatidylcholine, lysophosphatidylcholine, phosphatidylethanolamine and mixtures thereof.

The emulsifying component (b) may further contain one or more helper lipids selected from fatty acids, steroids, vitamins and mixtures thereof.

In the endocytosis enhancing component (c) said at least one compound inducing cellular uptake is selected from compounds that enhances cellular uptake via endocytosis. These compounds include, but are not limited to, transferrin, fragments and derivatives thereof and compounds having an analogous effect/activity; apolipoprotein A1, fragments and derivatives thereof and compounds having an analogous effect/activity; glycosylphosphatidylinositol (GIP)-anchored proteins, fragments and derivatives thereof and compounds having an analogous effect/activity; megalin-binding proteins, fragments and derivatives thereof and compounds having an analogous effect/activity; and atennapedia proteins, fragments and derivatives thereof and compounds having an analogous effect/activity. Particularly preferred is the iron transporting protein transferrin and fragments and derivatives thereof, notably human holotransferrin and fragments and derivatives thereof, which binds as the iron-loaded siderotransferrin to a specific receptor, which in turn induces endocytosis.

These transporting proteins are presented at the surface of perfluorcarbon nanocarrrier with variable substances attached to the surface to therewith enhance cellular endocytosis in vivo and in vitro.

A particularly preferred nanoemulsion of the invention comprises perfluoroocytlbromide as perfluorcarbon component (a), an emulsifying component (b) comprising phosphatidylcholine, sphingomyelin, cholesterol, lysophoshatidylcholine, DL-α-tocopherol and phosphatidylethanolamine as phospholipid, and transferrin as the endocytosis enhancing component (c).

The nanoemulsion of the invention is suitable for transfer of hydrophilic compounds, including pharmaceutics and genetic material, to target cells in vivo and in vitro, preferably the nanoemulsion is suitable for transfer of genetic material selected from RNA and DNA sequences and combinations and derivatives thereof, preferably is selected from all kinds of oligonucleotides, miRNA, siRNA, dsRNA and the like.

The nanoemulsion of the invention is particularly preferred for transfer of short interfering RNAs (siRNAs) identify a complementary sequence in mRNA and prevent it from being translated into protein or cause a cleavage of the mRNA by the protein complex. The corresponding genes are silenced by the use of these duplexes of RNA, which contain 21 to 23 nucleotides. When using siRNA for gene silencing the topical routes for administration and the selection of the vehicle are of major importance to gain effective intracellular concentrations of siRNA in intact living mammal cells and organs.

The method of aspect (4) of the invention for preparing the nanoemulsion of the invention includes the following steps
(a) preparing a buffered aqueous solution containing the emulsifying component,
(b) adjoining the perfluorcarbon component, and
(c) subsequent mixing, then homogenizing (e.g. by ultrasonication) and finally high pressure homogenization of the reaction product of step (b). For loading of the nanoemulsion with endocytosis enhancing component or with the hydrophilic compound the method further comprises one or more of the steps
(d) adding an aqueous solution of the endocytosis enhancing component and/or the hydrophilic compound (notably the genetic material) for transfer to the reaction product of step (c) and homogenizing (e.g. by ultrasonication) the resulting mixture.

The endocytosis enhancing component and the hydrophilic compound may be added in one single step (d) or in separate steps (d), they may also be included in the buffered aqueous solution of step (a).

The gene transfer agent or pharmaceutical composition of aspect (3) and the medicament of aspect (5) of the invention may encompass further pharmaceutically acceptable additives, carriers and the like.

To explain the mode of action and to demonstrate the effectiveness of the nanocarrier the use with transferrin as endocytosis enhancing substance is shown in the following "Examples".

The exemplary gene transfer is the application of an angiotensinogen siRNA which cause a distinct drop of the mean arterial blood pressure.

The invention is described in more detail in the following "Examples", which utilize transferrin as the endocytosis enhancing substance and short interfering RNA as genetic material. These examples are, however, not to be construed as limiting the invention.

EXAMPLES

Example 1

Preparation of a Perfluorcarbon/Transferrin Nanocarrier

For preparation of the perfluorcarbon nanocarrier, perfluoroocytlbromide (Perflubron) is emulsified with a mixture of phospholipids. One gram of the mixture contains phosphatidylcholine (980 mg), sphingomyelin (10 mg), cholesterol (5 mg), lysophoshatidylcholine (5 mg), in distilled water and 75 mM sodium dihydrogen phosphate ($NaH_2PO_4$) buffer. To gain 1000 µl of the perfluorcarbon nanocarrier, 475 µl perfluorooctylbromide, 36 mg phospholipids, 200 µl 75 mM $NaH_2PO_4$ at pH 7.4 and 325 µl distilled water are used.

First, phospholipids, sodium dihydrogen phosphate buffer and distilled water are mixed and subsequently the perfluorcarbon (PFC) solution is adjoined. Within 40 seconds, the composite has to be mixed by a shaker for 60 s and without any interruption homogenized twice by an ultrasonic device at a frequency of 1100 kHz for 120 s with intervals of 30 s. The sonication unit is kept at a temperature of 4° C. For the final emulsion of the otherwise insoluble PFC, the mixture is given into a high pressure homogenizer. Within six passages of homogenization at 2500 bar the milky composite turns into a transparent, bluish emulsion. This change to transparency is a macroscopic marker for the turn of the perfluorcarbon particles size below the visible wavelengths. The lowest visible wavelength (blue/violet) of λ=400 nm defines the particles size as λ/2 when the mixture becomes transparent. Four additional cycles of homogenization are added at this point. The particles size was measured in electron microscopy as 50 nm (mean) with all particles below 100 nm. To gain the functional nanocarrier, 4 mg holotransferrin is solved in 60 µl sterile 0.9% NaCl. Directly afterwards, the transferrin is homogenized for 2 s by the cooled ultrasonic device. The solved transferrin is added to 1000 μl perfluorcarbon emulsion to obtain an end concentration of 4 mg/ml. Again, the compound is directly put on a shaker for 30 s.

Example 2

Gene Transfer

Exemplary gene transfer: Renin is a hormone synthesized by the kidney in response to a blood pressure reduction. It transforms angiotensinogen to angiotensin 1, which is finally activated by angiotensin converting enzyme (ACE) to angiotensin 2. Angiotensin 2 is of major importance for middle term blood pressure regulation. Suppression of the angiotensinogen translation through siRNA delivered by the nanocarrier should cause similar blood pressure depression as a conventional ACE-blocker. For comparison of the effects, a group of animals were treated with the angiotensin converting enzyme blocker captopril. This small water-soluble substance was applied as intraperitoneal injection. Six hours after the injection, the effect on blood pressure was measured using a defined temperature regulated profile (see below)

Addition of siRNA: The transfer of siRNA into male CD1 mice is demonstrated. For usage in 35 g mice, 60 μg siRNA are solved in 30 μl isotonic NaCl directly prior to the in vivo investigations. The solution is added to 300 μl of the nanocarrier and homogenized at 4° C. by the ultrasonic device for 2 s.

Injection of nanocarrier and genetic material in the tail veins of mice: For general inhalation anesthesia the animals spontaneously breathed a mixture of Isoflurane in 63% $N_2O$, 35% $O_2$ and 2% $CO_2$ in a semiclosed system.

The compound consisting of siRNA and nanocarrier was injected into the tail vein under general inhalation anesthesia. To ensure stable cardiorespiratory conditions, the mice lay in a temperature regulated bed and were warmed by an infrared lamp. During and following the injection the respiratory frequency was monitored. Directly after the intravenous injection, the anesthesia was stopped and the animal recovered within the next two minutes.

Different sequences of angiotensinogen siRNA were commercially synthesized, and each was tested in a group of five animals. Controls received the complete nanocarrier either without siRNA or with non coding siRNA, a high flow injection of siRNA, or the siRNA in the PFC nanocarrier without transferrin.

Target of Gene transfer; Reduction of blood pressure following application of angiotensinogen siRNA: To evaluate whether the translation of angiotensinogen mRNA is successfully prevented, we measured the effect on the blood pressure regulation during a defined temperature profile (see below). Using a temperature regulated bed, it was possible to reduce the body temperature of the mice, so that the renin angiotensinogen system gets activated to keep the blood pressure stable. Inactivation of the functional renin angiotensin system causes a significant reduction of the blood pressure clearly visible during the temperature profile.

The animals underwent general inhalation anesthesia 24 hours after they had received the different described compounds by intravenous injection. The temperature-regulated bed was adjusted to 42° C., and thus the body temperature of the mice was kept stable during the initial 15 min of the measurement and the basal blood pressure was ascertained. After 15 min we adjusted the temperature of the bed to 30° C. Thereby the temperature of the heated bed continuously decreases, so that it reaches 30.5° C. thirty min after the blood pressure profile had started. At this point of time (30 min) the blood pressure was again measured. If the temperature of the bed had arrived at 30° C., it was than kept at this reduced temperature for 10 min. During this time period, the blood pressure was measured 5 min and 10 min after the temperature of the bed had reached 30° C. (35 min and 40 min after the profile was started). 10 min after the temperature of the bed attained 30° C. it was again adjusted to 42° C. The next blood pressure values were determined when the temperature of the bed attains 41.5° C., so at 47 min from the starting point of the profile. Accordingly, three more blood pressure values were assessed in intervals of five minutes, namely at 52 min, 57 min and 62 min after the blood pressure profile was initiated. The temperature profile of the heating bed is shown in Table 1.

TABLE 1

The temperature profile.

| Elapsed time after start of the profile [min] | Temperature of the bed |
|---|---|
| 15 | 42° C. |
| 30 | 30.5° C. |
| 35 | 30° C. |
| 40 | 30° C. |
| 43 | 41.5° C. |
| 47 | 42° C. |
| 52 | 42° C. |
| 57 | 42° C. |
| 62 | 42° C. |

Figure 1:
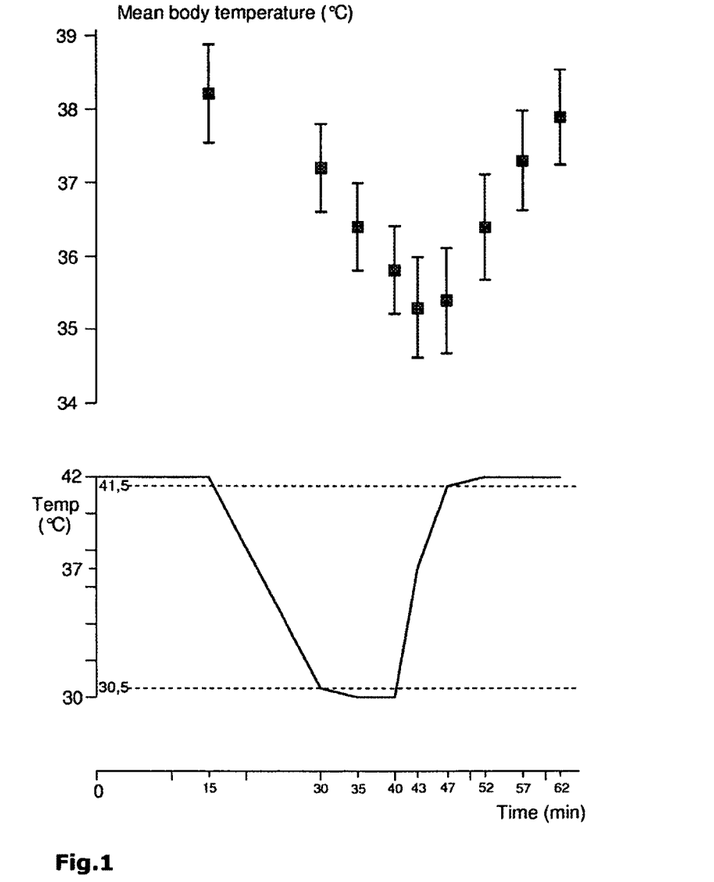

Results of exemplary gene transfer: To evaluate whether angiotensinogen siRNA is successfully delivered into the cells of a living animal, we induced a decrease of the blood pressure by a reduction of the animals body temperature using a temperature regulated bed. The temperature profile caused a significant decrease in the mean body temperature of the anaesthetized mice from 38° C. to 35° C. and a recovery after reheating the bed. FIG. 1 shows the mean body temperature following the described temperature profile in the warming unit.

For comparison with the effect of angiotensionogen siRNA on blood pressure, we studied the effect of the temperature profile in animals treated with the angiotensin converting enzyme blocker captopril, a common therapeutic option to suppress the renin angiotensin system in humans. Subsequently, the effect of the temperature profile was tested in animals which received angiotensinogen siRNA in the nanocarrier either containing the perfluorcarbon nanoemulsion and transferrin or solely the nanoemulsion. The data were compared to blood pressure values of control animals either treated with the nanocarrier, the nanocarrier and non coding siRNA or siRNA alone. The functional nanocarrier and the siRNA were well tolerated by the animals.

Figure 2:
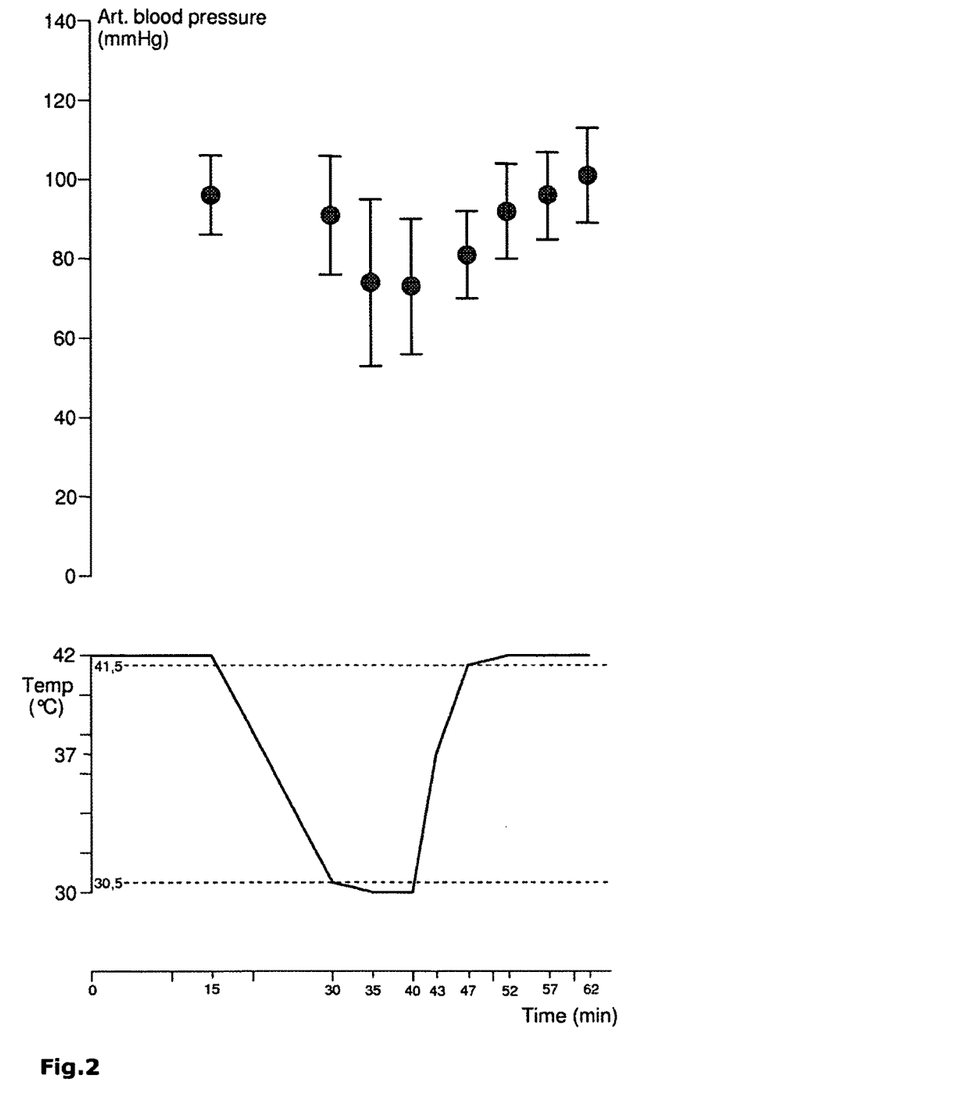

Blood pressure profile in untreated animals: FIG. 2 shows the mean arterial blood pressure of untreated mice.

Figure 3:
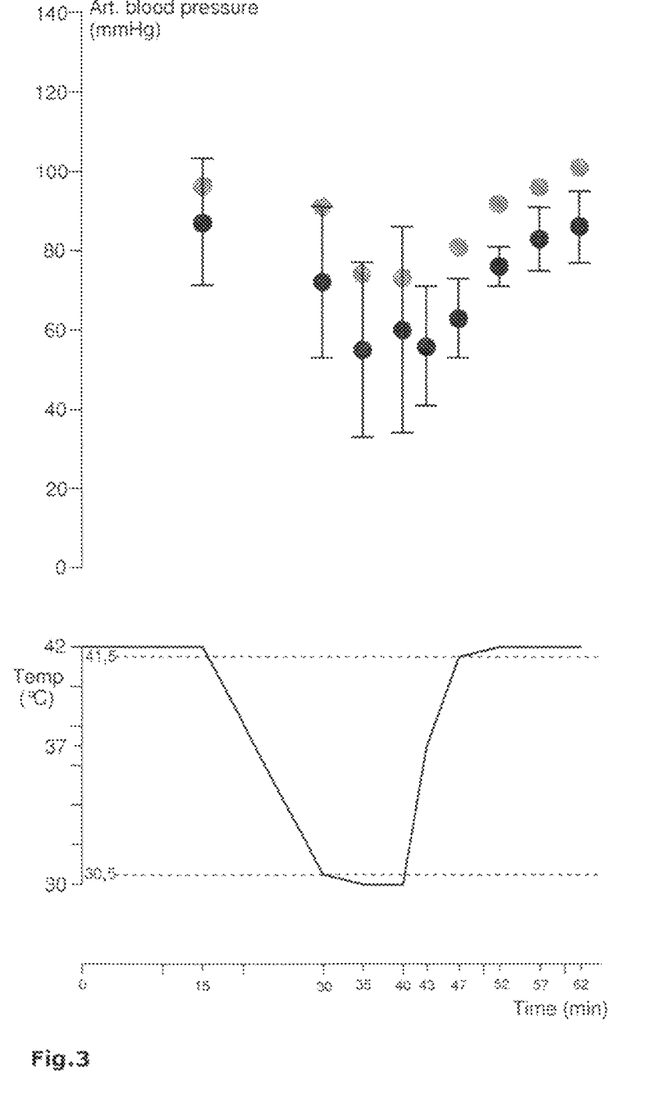
FIG. 3 shows the mean arterial blood pressure (±SD) 6-7 hours after application of the ACE-blocker Captopril (n=5, 10 mg/kg Captopril), grey dots=control values, black dots=actual values).

Blood pressure profile in animals treated with angiotensin converting enzyme blocker: Mice treated with the angiotensin converting enzyme blocker captopril have an impaired renin angiotensin system. We tested the effect of a reduced body temperature on blood pressure during a defined temperature profile. Thereby, a pronounced decrease of the blood pressure was documented five and ten minutes after the temperature of the bed had arrived at 30° C. In these animals recovery to normal basal blood pressure values occurred slowly, so that the animals had still low blood pressures at 52 min (FIG. 3).

Figure 4:
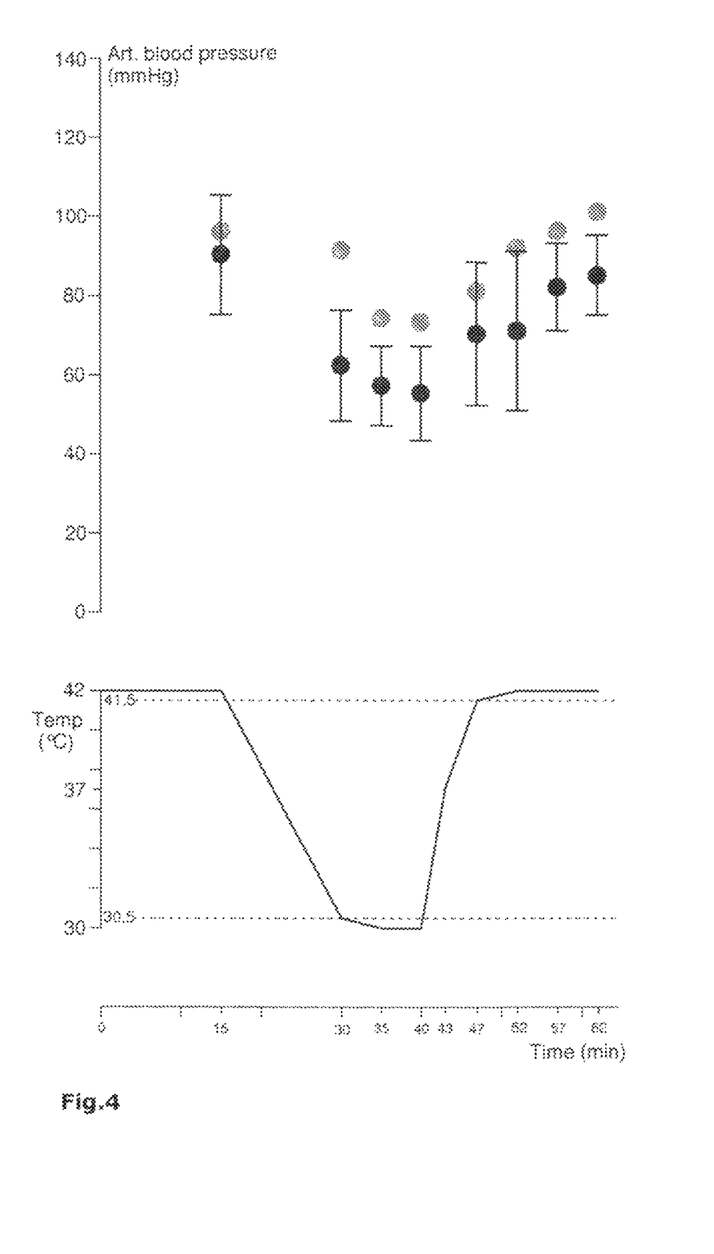
FIG. 4 shows the mean arterial blood pressure (±SD) 24 hours after application of the nanocarrier with angiotensinogen siRNA (n=5, 300 μl nanocarrier, 60 μg Agt siRNA, surface: transferrin protected by Fortecortin), grey dots=control values, black dots=actual values.

Blood pressure profile in mice after angiotensinogen siRNA delivery via the nanocarrier: The animals received the angiotensinogen siRNA sequence CCG GTT CTT GCC ACT GAG AAA (SEQ ID NO:1) delivered by the nanocarrier. By intravenous injection 60 µg siRNA were applied in 300 µl of the nanocarrier. An incubation period of 24 h allowed the siRNA to hinder the translation of angiotensiogen and thereby to affect the renin angiotensin system. Compared to controls the animals had impaired basal blood pressures and a distinct decrease of the blood pressure following the reduction of the body temperature. Moreover, the blood pressure remained at low values by the 57 min. Thus the measured blood pressure values were similar between animals treated with the angiotensin converting enzyme inhibitor and animals which received angiotensin siRNA delivered via the nanocarrier. FIG. 4 shows the reduction of arterial blood pressure following the siRNA induced inhibition of angiotensinogen.

Blood pressure profile in additional control animals: Four groups of controls received the composite displayed in Table 2. In these groups of animals as a response to a reduced body temperature the blood pressure was impaired at 35 and 40 minutes. The return to normal values of 37° C. to 42° C. leaded to a fast increase of blood pressure again so that the animals had normal basal values from 47 min until the profile ended. The observed blood pressure reduction related to a decreased body temperature was slight and recovery to normal basal values occurred directly after the temperature had reached normal values again, thus these profiles were similar to those of untreated animals (statistically not different).

TABLE 2

Procedures performed in groups of control animals.

Figure 5:
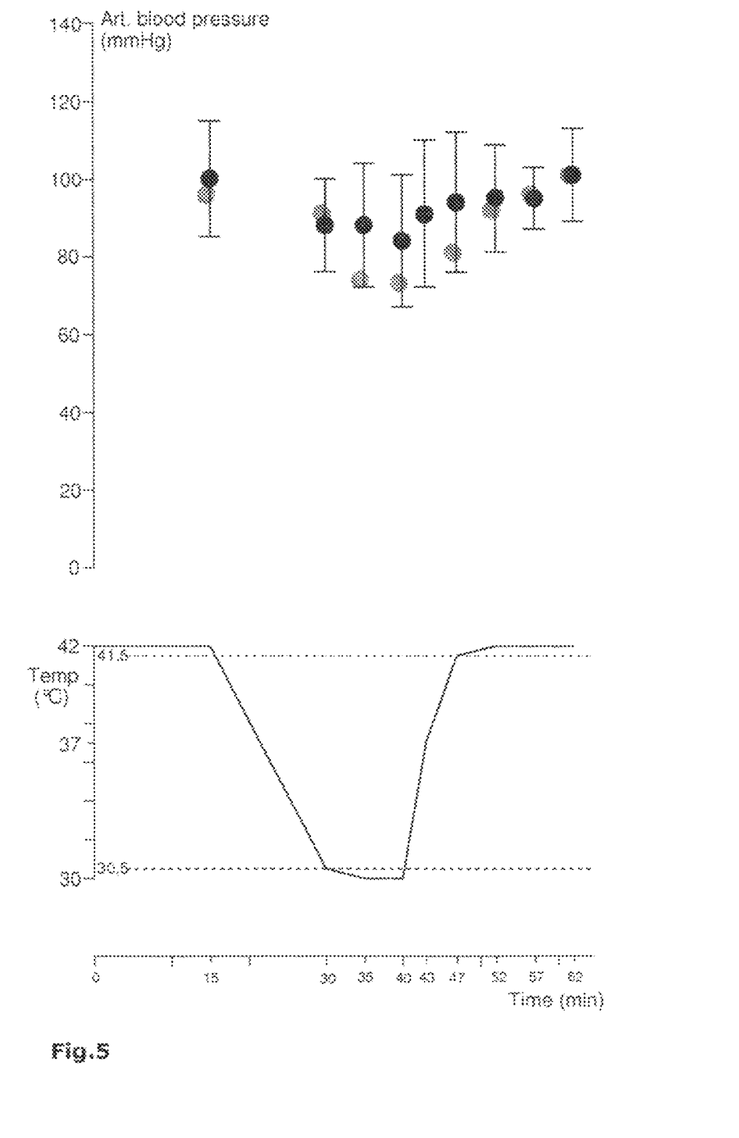
FIG. 5 shows the mean arterial blood pressure (±SD) 24 hours after application of angiotensinogen siRNA (n=5, 60 μg Agt siRNA) without nanocarrier injected within 2 seconds "Hydrodynamic transfection", grey dots=control values, black dots=actual values.
Figure 7:
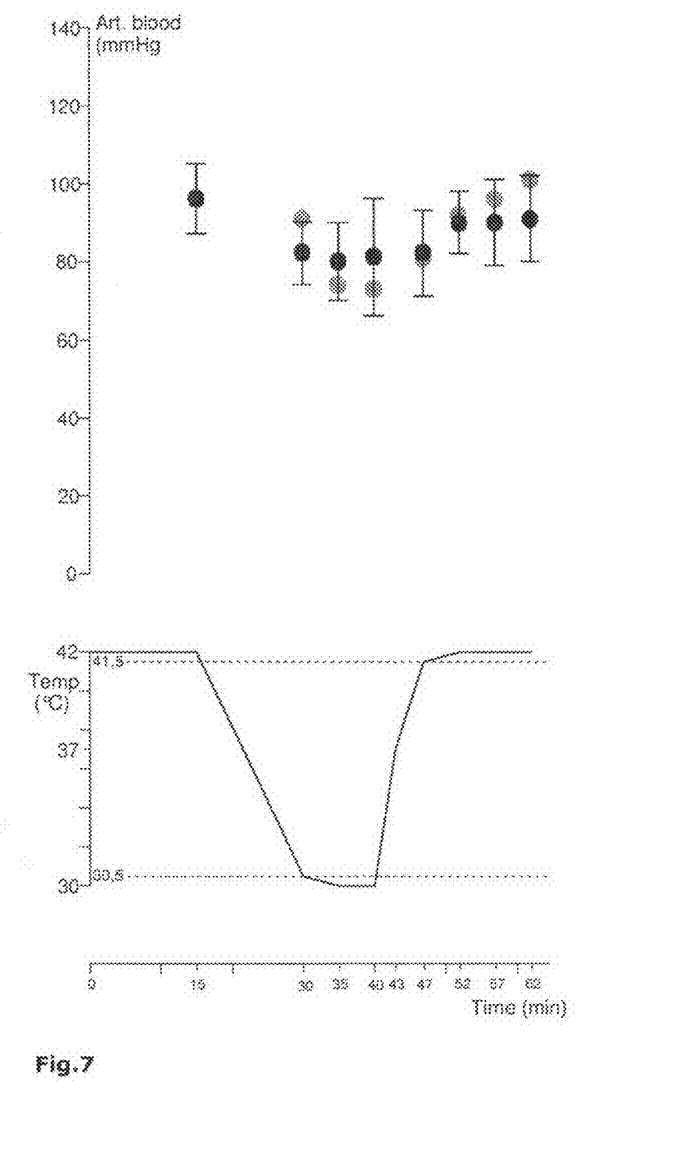
FIG. 7 shows the mean arterial blood pressure (±SD) 24 hours after application of the a non-coding siRNA using the nanocarrier (n=5, 300 μl nanocarrier, 60 μg Agt siRNA, surface: transferrin protected by Fortecortin), grey dots=control values, the black dots=actual values).
Figure 8:
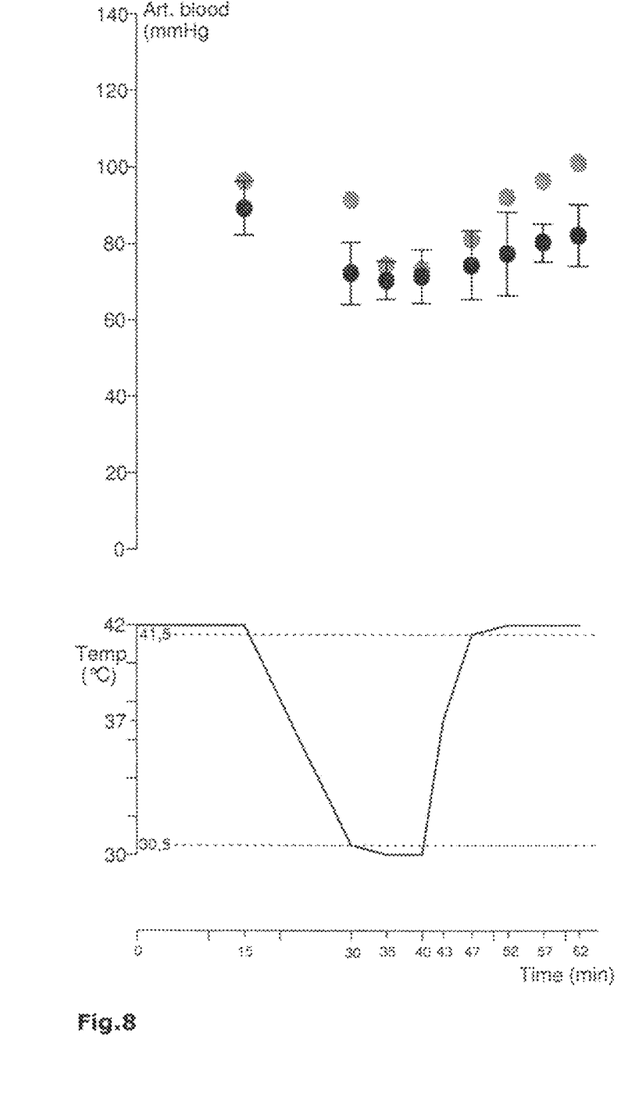
FIG. 8 shows the mean arterial blood pressure (±SD) 24 hours after application of the nanocarrier only (n=5, 300 μl nanocarrier, 60 μg Agt siRNA, surface: transferrin protected by Fortecortin), grey dots=control values, black dots=actual values).
Figure 9:
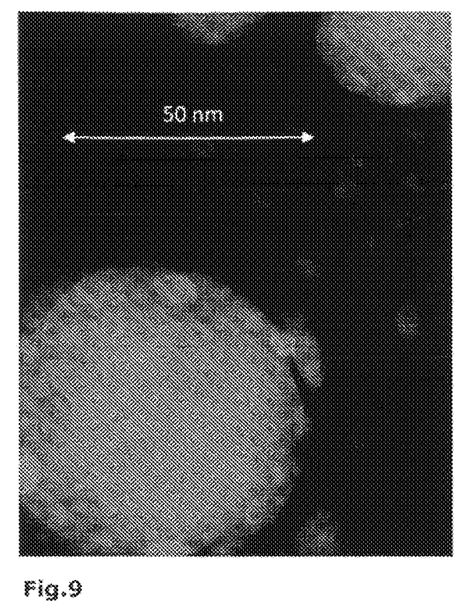
FIG. 9: Electron microscopic image showing a particle of the nanocarrier. The particle has a size of about 50 nanometres.
Figure 10:
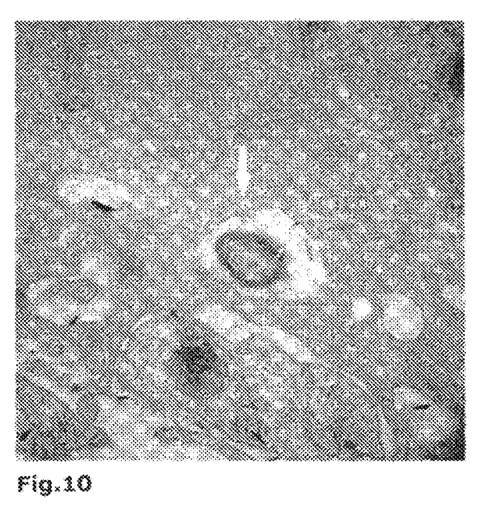
FIG. 10: The image shows a hepatocyte at 46.000-fold magnification. The liver was explanted 30 minutes after intravenous injection of nanocarrier containing siRNA. The arrow marks an endosome after receptor-mediated endocytosis containing a particle of the nanocarrier loaded with siRNA. The membrane and free space around the particle beside the cell surface documents that uptake occurs by receptor-mediated endocytosis.
Figure 11:
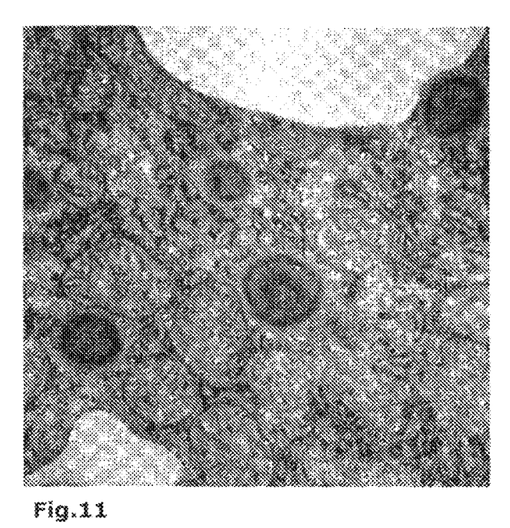
FIG. 11: Electron microscopic image of a hepatocyte at 50.000-fold magnification. Two hours after intravenous administration of nanocarrier and siRNA the liver was explanted. Round vesicles of the nanocarrier containing dark structures without surrounding membranes are visible. Unlike the nanocarrier vesicles in the image of FIG. 10, the particles are not covered by a membrane. Obviously, all visible nanocarrier were liberated into the cytosol.
Figure 12:
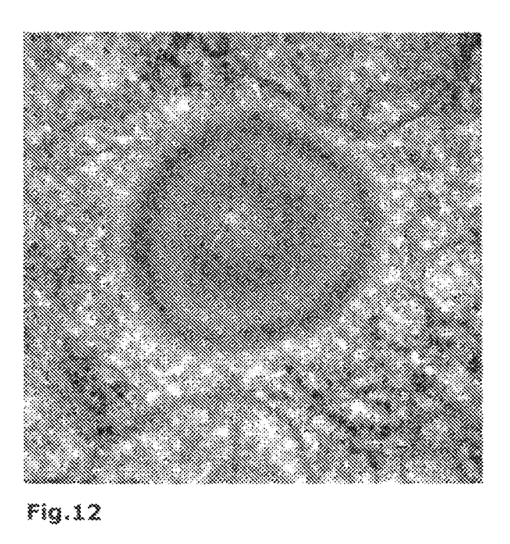
FIG. 12: Enlarged detail of the electron microscopic section displayed in FIG. 10. At 175.000-fold magnification a particle of siRNA-loaded nanocarrier liberated into the cytoplasm of the hepatocyte is shown. The dark structures within the particle also visible in FIGS. 10 and 11 correspond to the incorporated siRNA.
Figure 13:
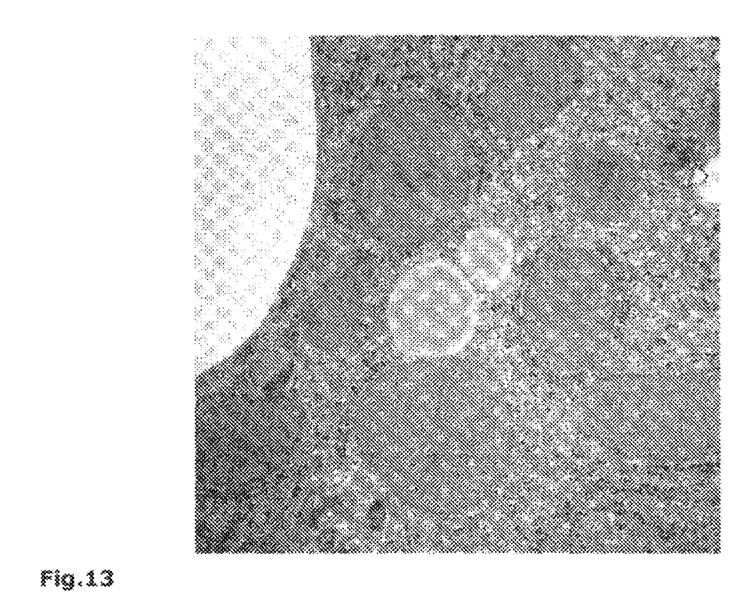
FIG. 13: Electron microscopic image of a hepatocyte at 50.000-fold magnification. Four hours following intravenous injection, the animal was sacrificed and the liver was extracted. At this time point the nanocarrier does not longer contain the dark structures visible in FIGS. 10 to 12. Very probably the siRNA delivered by the nanocarrier was set free into the cytoplasm.

| Procedure | Result |
| --- | --- |
| Angiotensinogen siRNA without nanocarrier injection within 2 s"Hydrodynamic transfection" | Blood pressure profile comparable to untreated animals (FIG. 5) |
| Incomplete Nanocarrier Nanocarrier and siRNA without endocytosis enhancing transferrin at the surface | Blood pressure profile comparable to untreated animals (FIG. 6) |
| Non-coding siRNA Nanocarrier with a non-coding siRNA sequence | Blood pressure profile comparable to untreated animals (FIG. 7) |
| Nanocarrier only Nanocarrier without siRNA | Blood pressure profile comparable to untreated animals (FIG. 8) |

Figure 6:
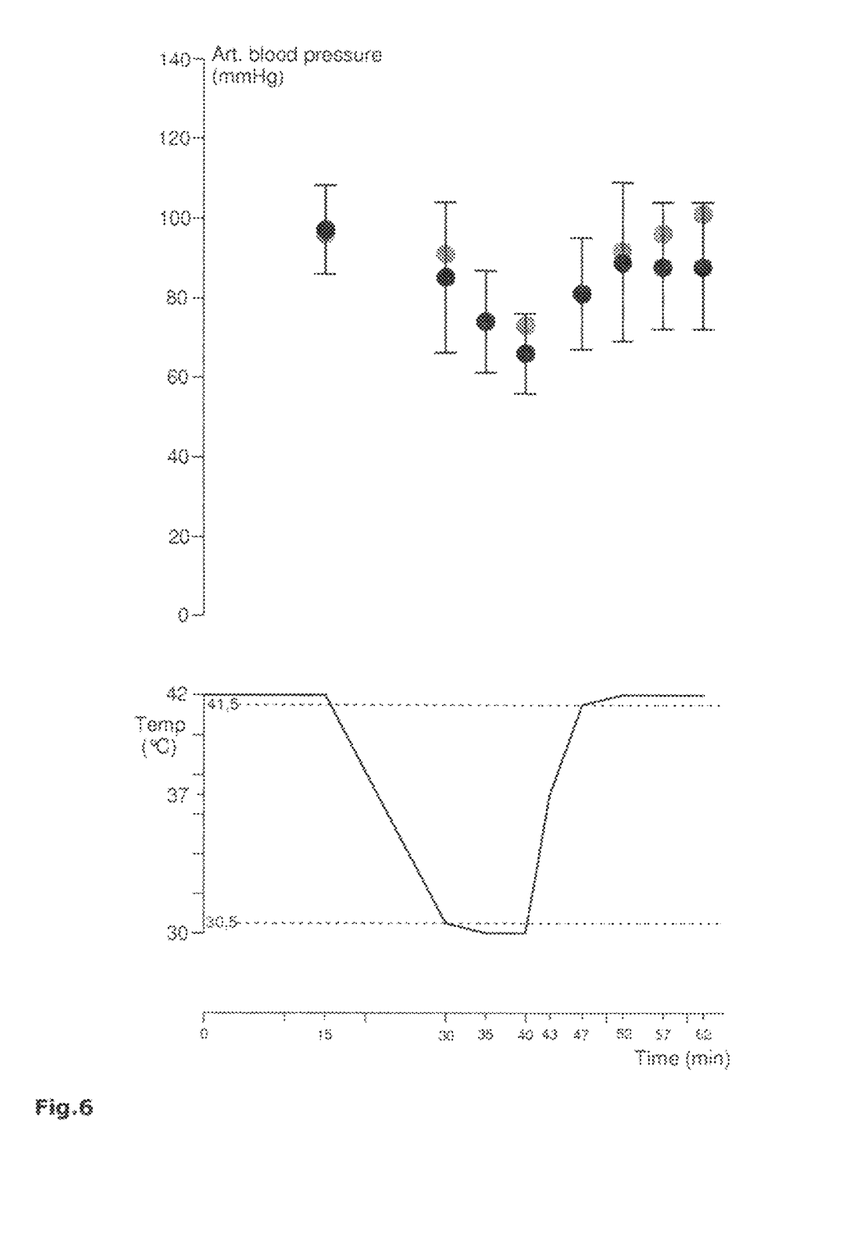
FIG. 6 shows the mean arterial blood pressure (±SD) 24 hours after application of the angiotensinogen siRNA using an incomplete nanocarrier, the surface of the nanocarrier is without the endocytosis enhancing protein transferrin (n=5, 300 μl nanocarrier, 60 μg Agt siRNA, surface: no transferrin, addition of Fortecortin), grey dots=control values, black dots=actual values.

Perfluorcarbon-nanoemulsion, not doted with endocytosis enhancing molecules: The experimental data on a perfluocarbon nanoemulsion not doted with an endocytosis enhancing surface are shown in FIG. 6 for the exemplary use of siRNA directed against the blood pressure regulating renin angiotensinogen system. The blood pressure profiles of animals treated with perfluorcarbon nanoemulsion not doted with an endocytosis enhancing surface were compared to the blood pressure profiles of control animals. This experimental data demonstrate that perfluorocarbon nanoemulsions not doted with endocytosis enhancing surfaces are not functional for the delivery of genetic material into the cells of living animals as the blood pressure profiles of the animals receiving this substance were significantly not different to the blood pressure profiles of the controls.

Electron microscopic visualization of the angiotensinogen siRNA delivery into hepatocytes of mice: Mice weighing 35 g received tail vein injections of the nanocarrier loaded with the angiotensiogen siRNA. After intervals of 30 minutes, and 2 respectively 4 hours, the animals were sacrificed and the liver was explanted. The liver tissue was epoxy resin embedded, and thin sections were obtained by means of a microtome. Electron microscopy of these sections revealed convincingly a special appearance of the nanoparticles incorporated into cells. The efficiency of the nanocarrier for delivery of siRNA into intact organs of living animals was demonstrated in electron microscopic images: Within the first 30 minutes the nanocarrier was incorporated into intracellular endosomes via receptor-mediated uptake. During the first two hours after injection, the nanocarrier was leaving the endosome and was liberated into the cytoplasm. Following the next two hours, electron dense structures of the nanocarrier were no longer visible, implying very probably the unload of transported siRNA and its liberation into the cytosol.

The electron microscopic images depicted in FIGS. 9 to 13 show the nanocarrier's structure and document its receptor-mediated uptake, liberation from the intracellular endosomes and unloading of delivered siRNA after intravenous injection in living mice.

FIGS. 10 to 13 display electron microscopic images of cross sections from liver tissue of mice.

SEQUENCE LISTING, FREE TEXT

SEQ ID NO: 1 angiotensinogen siRNA sequence

The invention claimed is:

1. A stable perfluorcarbon nanoemulsion having an endocytosis enhancing surface, said nanoemulsion comprising:
   (i) a perfluorcarbon component comprising perfluorocytlbromide;
   (ii) an emulsifying component comprising phosphatidylcholine, sphingomyelin, cholesterol and lysophosphatidylcholine as a phospholipid; and
   (iii) transferrin as an endocytosis enhancing component that induces cellular uptake of the nanoemulsion endocytosis;
wherein said nanoemulsion has a buffered discontinuous aqueous phase representing 25 to 60% of the microemulsion and wherein said microemulsion has a particle size of below 100 nm.

2. The nanoemulsion of claim 1, which is suitable for transfer of hydrophilic compounds to cells in vivo and in vitro.

3. A gene-transfer agent or a pharmaceutical composition comprising a nanoemulsion of claim 1.

4. The gene-transfer agent or pharmaceutical composition of claim 3, which further comprises pharmaceutics and genetic material to be transferred to cells in vivo and in vitro.

* * * * *